United States Patent
Zierhofer

(10) Patent No.: US 8,428,742 B2
(45) Date of Patent: Apr. 23, 2013

(54) SIMULTANEOUS STIMULATION FOR LOW POWER CONSUMPTION

(75) Inventor: Clemens M. Zierhofer, Kundl (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 212 days.

(21) Appl. No.: 12/957,974

(22) Filed: Dec. 1, 2010

(65) Prior Publication Data

US 2011/0077711 A1    Mar. 31, 2011

Related U.S. Application Data

(60) Division of application No. 11/101,149, filed on Apr. 7, 2005, now Pat. No. 7,917,224, which is a continuation-in-part of application No. 10/303,568, filed on Nov. 25, 2002, now Pat. No. 7,209,789, which is a continuation of application No. 09/648,687, filed on Aug. 25, 2000, now Pat. No. 6,594,525, said application No. 11/101,149 is a continuation-in-part of application No. 10/361,386, filed on Feb. 10, 2003, now Pat. No. 7,382,850, which is a division of application No. 09/621,444, filed on Jul. 21, 2000, now Pat. No. 6,600, 955.

(60) Provisional application No. 60/150,773, filed on Aug. 26, 1999, provisional application No. 60/144,799, filed on Jul. 21, 1999.

(51) Int. Cl.
*A61N 1/32* (2006.01)

(52) U.S. Cl.
USPC .......................................................... 607/57

(58) Field of Classification Search .............. 607/55–57, 607/137; 623/10
See application file for complete search history.

(56) References Cited

U.S. PATENT DOCUMENTS

| | | | |
|---|---|---|---|
| 3,918,042 A | 11/1975 | Werner | 340/347 AD |
| 4,284,856 A | 8/1981 | Hochmair et al. | 179/107 E |

(Continued)

FOREIGN PATENT DOCUMENTS

| | | |
|---|---|---|
| EP | 1854504 | 11/2007 |
| EP | 2208507 | 7/2010 |

(Continued)

OTHER PUBLICATIONS

Chakravarthy, C. V. "An amplitude-controlled adaptive delta sigma modulator", The Radio and Electronic Engineer, vol. 49, No. 1, pp. 49-54, Jan. 1979.

(Continued)

*Primary Examiner* — Christopher D Koharski
*Assistant Examiner* — Frances Oropeza
(74) *Attorney, Agent, or Firm* — Sunstein Kann Murphy & Timbers LLP

(57) ABSTRACT

A stimulation system including a stimulator having a multi-channel electrode array utilizing a monopolar electrode configuration. A processor is operatively coupled to the stimulator. The processor is configured to determine a channel interaction (CI) sequence using simultaneous, sign-correlated pulses and channel interaction compensation. The CI sequence has a CI pulse rate and a CI mean pulse amplitude, and produces resulting potentials that are substantially equal to desired potentials at given positions relative to the multi-channel array. The CI sequence may include temporal gaps between pulses, wherein the processor may be configured to increase the CI pulse rate, such that the temporal gap between pulses is decreased. Furthermore, the processor may be configured to reduce the pulse amplitude of the CI sequence while increasing pulse phase duration, such that charge per pulse remains substantially unchanged and the temporal gap between pulses is decreased.

31 Claims, 7 Drawing Sheets

U.S. PATENT DOCUMENTS

| | | | | |
|---|---|---|---|---|
| 4,428,377 | A | 1/1984 | Zollner et al. | 128/419 R |
| 4,515,158 | A | 5/1985 | Patrick et al. | 128/419 R |
| 4,940,977 | A | 7/1990 | Mandell | 341/143 |
| 5,151,158 | A | 9/1992 | Bowen et al. | 128/419 R |
| 5,215,085 | A | 6/1993 | Von Wallenberg-Pachaly | 128/420.6 |
| 5,549,658 | A | 8/1996 | Shannon et al. | 607/57 |
| 5,601,617 | A | 2/1997 | Loeb et al. | 607/56 |
| 5,609,616 | A | 3/1997 | Schulman et al. | 607/56 |
| 5,749,912 | A | 5/1998 | Zhang et al. | 607/57 |
| 5,824,022 | A | 10/1998 | Zilberman et al. | 607/57 |
| 5,938,691 | A | 8/1999 | Schulman et al. | 607/57 |
| 5,957,958 | A | 9/1999 | Schulman et al. | 607/56 |
| 5,974,342 | A * | 10/1999 | Petrofsky | 607/50 |
| 6,002,966 | A | 12/1999 | Loeb et al. | 607/57 |
| 6,175,767 | B1 | 1/2001 | Doyle, Sr. | 607/57 |
| 6,219,580 | B1 | 4/2001 | Faltys et al. | 607/57 |
| 6,289,247 | B1 | 9/2001 | Faltys et al. | 607/57 |
| 6,295,472 | B1 | 9/2001 | Rubinstein et al. | 607/55 |
| 6,594,525 | B1 | 7/2003 | Zierhofer | 607/57 |
| 6,600,955 | B1 | 7/2003 | Zierhofer | 607/57 |
| 7,917,224 | B2 | 3/2011 | Zierhofer | 607/57 |
| 2001/0031909 | A1 | 10/2001 | Faltys et al. | 600/25 |
| 2004/0082985 | A1 | 4/2004 | Faltys et al. | 607/116 |
| 2009/0036962 | A1 | 2/2009 | Zierhofer | 607/137 |

FOREIGN PATENT DOCUMENTS

| | | |
|---|---|---|
| WO | WO 98/49775 | 11/1998 |
| WO | WO 99/35882 | 7/1999 |
| WO | WO 99/49815 | 10/1999 |
| WO | WO 01/13991 | 3/2001 |
| WO | WO 01/19304 | 3/2001 |
| WO | WO 2005/113064 | 12/2005 |
| WO | WO 2006/136961 | 12/2006 |

OTHER PUBLICATIONS

Jaggi, et al., "Instantaneously Adaptive Delta Sigma Modulator Modulateur Delta Sigma Instantanement Adaptatif", Can. Elect. Eng. J., vol. 11, No. 1, 4 Pages (1986).

Kral et al., "Spacial Resolution of Cochlear Implants: The Electrical Field and Excitation of Auditory Afferents", Hearing Research, 121:11-28, 1998.

Liang et al., "A Method for Evaluating the Selectivity of Electrodes Implanted for Nerve Simulation" IEEE Transactions on Biomedical Engineering, vol. 38 No. 5, pp. 443-449, May 1991.

Loizou, "Signal Processing for Cochlear Prosthesis: A Tutorial Review," IEEE, vol. 2, pp. 881-885, 1997.

Matsuoka, "Compound Action Potentials Evoked by Electrical Pulse Trains: Effects of Stimulus Parameters on Response Patterns", Thesis at University of Iowa, Jul. 1998.

Wilson et al., "Better Speech Recognition with Cochlear Implants", Nature, 352:236-238, Jul. 1991.

Wilson et al., "Speech Processors for Auditory Prostheses", Seventh Quarterly Progress Report, Feb. 1 through Apr. 30, 1994, NIH Contract N01-DC-2-24-1.

International Searching Authority, International Search Report—International Application No. PCT/IB00/01338, dated Dec. 14, 2000, 5 pages.

International Searching Authority, International Search Report—International Application No. PCT/IB2005/002349, dated Nov. 16, 2005, together with the Written Opinion of the International Searching Authority, 14 pages.

International Searching Authority, International Search Report—International Application No. PCT/IB2006/002510, dated Jan. 23, 2007, together with the Written Opinion of the International Searching Authority, 14 pages.

European Patent Office, Partial European Search Report—Application No. 07075655.6-2305—dated Nov. 5, 2008, 7 pages.

European Patent Office, European Search Report—European Application No. EP 10003323.2-2305, dated Jun. 22, 2010, 6 pages.

European Patent Office, Examination Report—European Application No. 07075655.6-2305, dated Aug. 26, 2010, 4 pages.

European Patent Office, Communication Pursuant to Article 94(3) EPC—European Application No. 07075655.6-2305, dated Jun. 8, 2009, 1 page.

Clive Froud & Co Limited, Response dated Oct. 12, 2009, pertaining to European Application No. 07075655.6-2305, 6 pages.

United States Patent and Trademark Office, Office Action dated Jan. 3, 2002, pertaining to U.S. Appl. No. 09/648,687, 13 pages.

Bromberg & Sunstein LLP, Response dated Apr. 2, 2002, pertaining to U.S. Appl. No. 09/648,687, 14 pages.

United States Patent and Trademark Office, Office Action dated Jun. 26, 2002, pertaining to U.S. Appl. No. 09/648,687, 7 pages.

Bromberg & Sunstein LLP, Response dated Sep. 11, 2002, pertaining to U.S. Appl. No. 09/648,687, 5 pages.

United States Patent and Trademark Office, Interview Summary dated Sep. 16, 2002, pertaining to U.S. Appl. No. 09/648,687, 10 pages.

United States Patent and Trademark Office, Advisory Action and Interview Summary dated Oct. 1, 2002, pertaining to U.S. Appl. No. 09/648,687, 6 pages.

Bromberg & Sunstein LLP, Amendment dated Nov. 25, 2002, pertaining to U.S. Appl. No. 09/648,687, 12 pages.

United States Patent and Trademark Office, Interview Summary dated Dec. 9, 2002, pertaining to U.S. Appl. No. 09/648,687, 2 pages.

United States Patent and Trademark Office, Notice of Allowance and Fee(s) Due dated Dec. 16, 2002, pertaining to U.S. Appl. No. 09/648,687, 9 pages.

Bromberg & Sunstein LLP, Election and Preliminary Amendment dated Mar. 3, 2006, pertaining to U.S. Appl. No. 10/303,568, 6 pages.

United States Patent and Trademark Office, Office Action dated Mar. 31, 2006, pertaining to U.S. Appl. No. 10/303,568, 11 pages.

Bromberg & Sunstein LLP, Response dated Sep. 28, 2006, pertaining to U.S. Appl. No. 10/303,568, 8 pages.

United States Patent and Trademark Office, Interview Summary dated Oct. 6, 2006, pertaining to U.S. Appl. No. 10/303,568, 4 pages.

United States Patent and Trademark Office, Notice of Allowance and Fee(s) Due dated Dec. 19, 2006, pertaining to U.S. Appl. No. 10/303,568, 5 pages.

United States Patent and Trademark Office, Office Action dated Jan. 31, 2008, pertaining to U.S. Appl. No. 11/101,149, 5 pages.

Bromberg & Sunstein LLP, Response dated Feb. 29, 2008, pertaining to U.S. Appl. No. 11/101,149, 6 pages.

United States Patent and Trademark Office, Office Action dated May 16, 2008, pertaining to U.S. Appl. No. 11/101,149, 10 pages.

Bromberg & Sunstein LLP, Response dated Aug. 15, 2008, pertaining to U.S. Appl. No. 11/101,149, 7 pages.

United States Patent and Trademark Office, Office Action dated Dec. 16, 2008, pertaining to U.S. Appl. No. 11/101,149, 12 pages.

Bromberg & Sunstein LLP, Response After Final Rejection dated Mar. 16, 2009, pertaining to U.S. Appl. No. 11/101,149, 8 pages.

United States Patent and Trademark Office, Advisory Action dated Apr. 1, 2009, pertaining to U.S. Appl. No. 11/101,149, 3 pages.

Bromberg & Sunstein LLP, Request for Continued Examination dated May 15, 2009, pertaining to U.S. Appl. No. 11/101,149, 12 pages.

United States Patent and Trademark Office, Office Action dated Jul. 30, 2009, pertaining to U.S. Appl. No. 11/101,149, 9 pages.

Sunstein Kann Murphy & Timbers LLP, Response dated Oct. 29, 2009, pertaining to U.S. Appl. No. 11/101,149, 13 pages.

United States Patent and Trademark Office, Office Action dated Mar. 4, 2010, pertaining to U.S. Appl. No. 11/101,149, 8 pages.

United States Patent and Trademark Office, Interview Summary dated Mar. 24, 2010, pertaining to U.S. Appl. No. 11/101,149, 4 pages.

United States Patent and Trademark Office, Interview Summary dated Jul. 30, 2010, pertaining to U.S. Appl. No. 11/101,149, 4 pages.

Sunstein Kann Murphy & Timbers LLP, Response to Restriction Requirement dated Apr. 30, 2010, pertaining to U.S. Appl. No. 11/685,887, 7 pages.

United States Patent and Trademark Office, Office Action dated Aug. 2, 2010, pertaining to U.S. Appl. No. 11/685,887, 6 pages.

European Patent Office, Extended European Search Report, Application No. EP 11 16 5881, Jul. 13, 2011, 7 pages.

\* cited by examiner

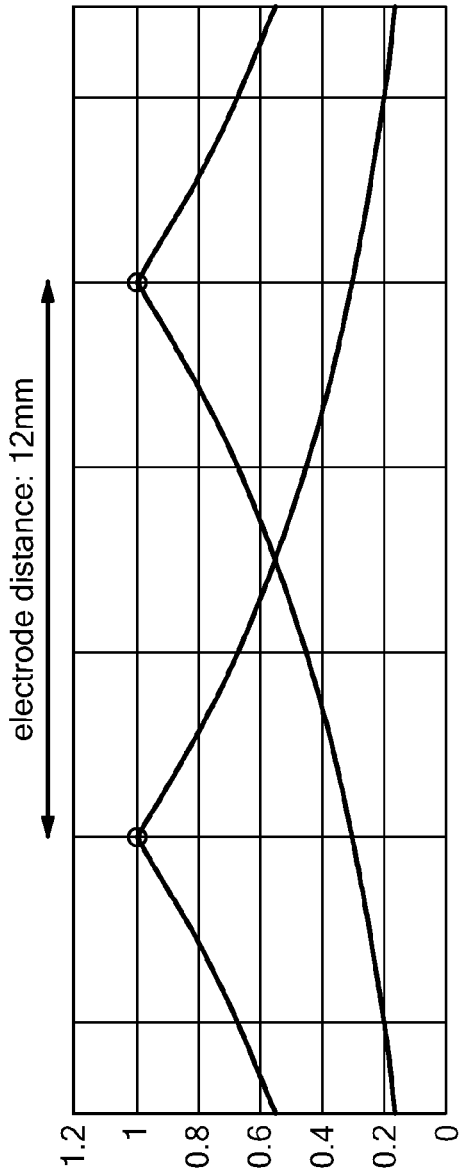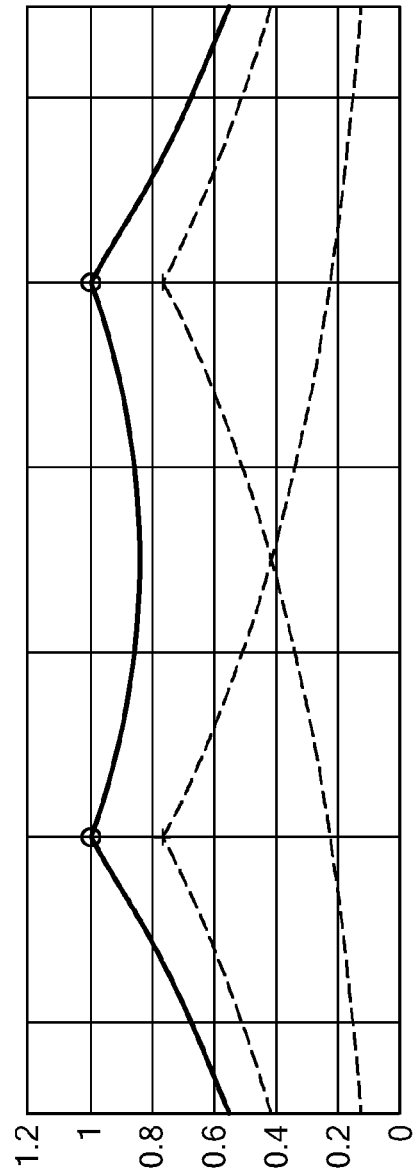
FIG. 5(a)
FIG. 5(b)

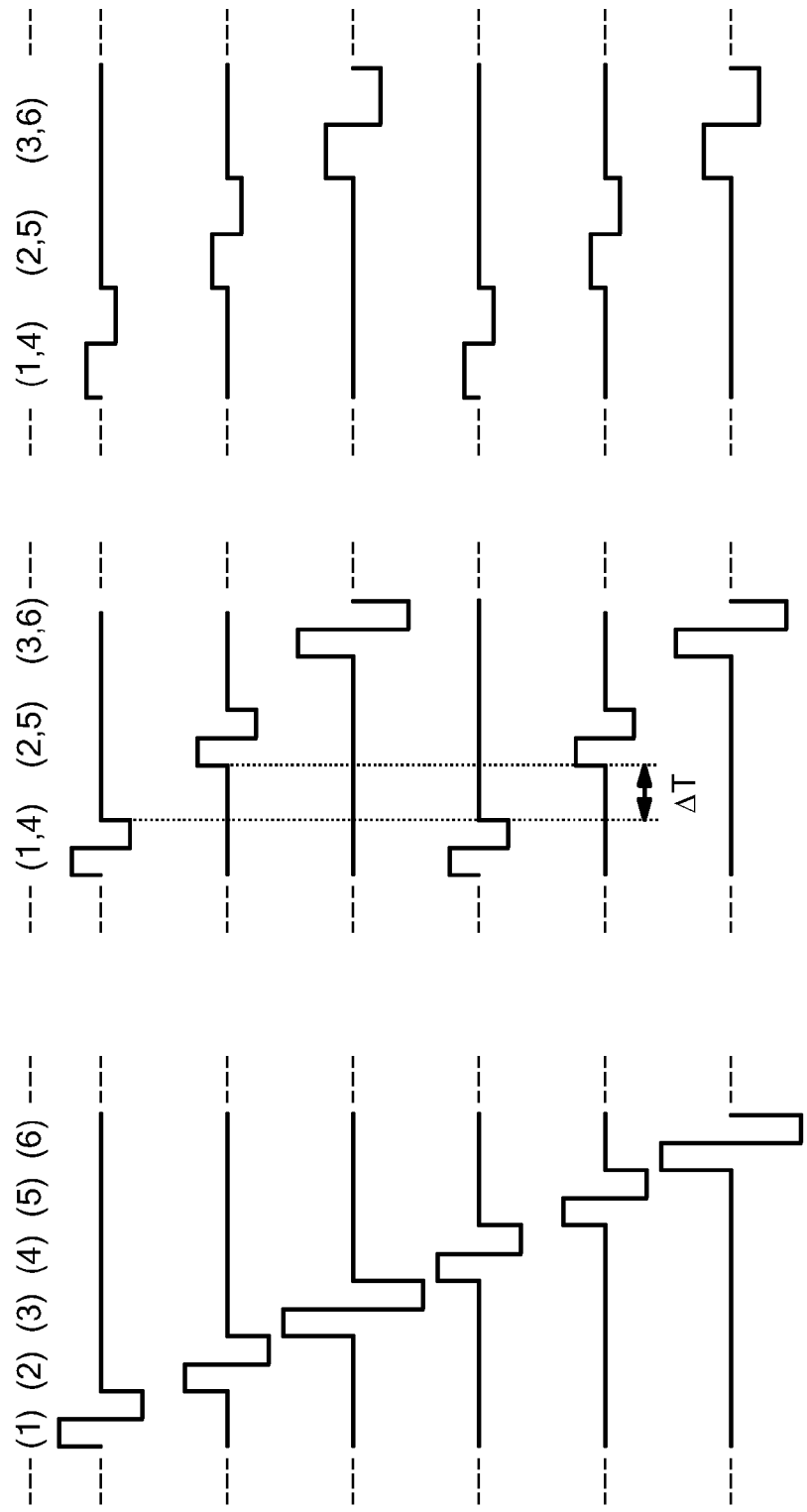

SIMULTANEOUS STIMULATION FOR LOW POWER CONSUMPTION

CROSS REFERENCE TO RELATED APPLICATIONS

This application is a divisional of U.S. patent application Ser. No. 11/101,149, filed Apr. 7, 2005, entitled "Simultaneous Stimulation for Low Power Consumption," issued as U.S. Pat. No. 7,917,224, which in turn is a continuation-in-part of U.S. patent application Ser. No. 10/303,568, filed Nov. 25, 2002, entitled "Electrical Nerve Stimulation Based on Channel Specific Sampling Sequences" issued as U.S. Pat. No. 7,209,789, which is a continuation of U.S. patent application Ser. No. 09/648,687 filed Aug. 25, 2000, entitled "Electrical Nerve Stimulation Based on Channel Specific Sampling Sequences," issued as U.S. Pat. No. 6,594,525, which claims priority from U.S. Provisional Patent Application Ser. No. 60/150,773 filed Aug. 26, 1999, entitled "Concept for Electrical Stimulation of the Acoustic Nerve Based on Channel Specific Sampling Sequences (CSSS)." Additionally, U.S. patent application Ser. No. 11/101,149 is a continuation-in-part of U.S. patent application Ser. No. 10/361,386, filed Feb. 10, 2003, entitled "Multi-channel Cochlear Implant with Neural Response Telemetry," issued as U.S. Pat. No. 7,382,850, which is a divisional of U.S. patent application Ser. No. 09/621,444, filed Jul. 21, 2000, entitled "Multi-channel Cochlear Implant with Neural Response Telemetry," issued as U.S. Pat. No. 6,600,955, which claims priority from U.S. Provisional Patent Application Ser. No. 60/144,799, filed Jul. 21, 1999, entitled "Multi-channel Cochlear Implant with Neural Response Telemetry." Each of the above-described applications are hereby incorporated herein by reference, in their entirety.

TECHNICAL FIELD

The present invention relates to electrical nerve stimulation, and more particularly, electrostimulation of the nerve based on channel specific sampling sequences.

BACKGROUND ART

Cochlear implants (inner-ear prostheses) are a possibility to help profoundly deaf or severely hearing impaired persons. Unlike conventional hearing aids, which just apply an amplified and modified sound signal, a cochlear implant is based on direct electrical stimulation of the acoustic nerve. The intention of a cochlear implant is to electrically stimulate neural structures in the inner ear in such a way that a hearing sensation most similar to normal hearing is obtained.

FIG. 1 shows a conventional cochlear prosthesis. The cochlear prosthesis essentially consists of two parts, the speech processor 101 that is typically positioned externally proximate the ear, and the implanted stimulator 105. The speech processor 101 includes the power supply (batteries) of the overall system and is used to perform signal processing of the acoustic signal to extract the stimulation parameters. The stimulator 105 generates the stimulation patterns and conducts them to the nerve tissue by means of an electrode array 107 that extends into the scala tympani 109 in the inner ear. The connection between speech processor and stimulator is established either by means of a radio frequency link (transcutaneous) using primary coils 103 and secondary coils within stimulator 105, or by means of a plug in the skin (percutaneous).

One successful stimulation strategy is the so called "continuous-interleaved-sampling strategy" (CIS), as described by Wilson B. S., Finley C. C., Lawson D. T., Wolford R. D., Eddington D. K., Rabinowitz W. M., "Better speech recognition with cochlear implants," Nature, vol. 352, 236-238 (July 1991) [hereinafter Wilson et al., 1991], which is incorporated herein by reference. Signal processing for CIS in the speech processor involves the following steps:

a. splitting up of the audio frequency range into spectral bands by means of a filter bank,
 b. envelope detection of each filter output signal, and
 c. instantaneous nonlinear compression of the envelope signal (map law).

According to the tonotopic organization of the cochlea, each stimulation electrode in the scala tympani is associated with a band pass filter of the external filter bank. For stimulation, symmetrical biphasic current pulses are applied. The amplitudes of the stimulation pulses are directly obtained from the compressed envelope signals (step (c) of above). These signals are sampled sequentially, and the stimulation pulses are applied in a strictly non-overlapping sequence. Thus, as a typical CIS-feature, only one stimulation channel is active at one time. The overall stimulation rate is comparatively high. For example, assuming an overall stimulation rate of 18 kpps, and using a 12-channel filter bank, the stimulation rate per channel is 1.5 kpps. Such a stimulation rate per channel usually is sufficient for adequate temporal representation of the envelope signal.

The maximum overall stimulation rate is limited by the minimum phase duration per pulse. The phase duration cannot be chosen arbitrarily short, because the shorter the pulses, the higher the current amplitudes have to be to elicit action potentials in neurons, and current amplitudes are limited for various practical reasons. For an overall stimulation rate of 18 kpps, the phase duration is 27 μs, which is at the lower limit.

Each output of the CIS band pass filters can roughly be regarded as a sinusoid at the center frequency of the band pass filter, which is modulated by the envelope signal. This is due to the quality factor Q=3 of the filters. In case of a voiced speech segment, this envelope is approximately periodic, and the repetition rate is equal to the pitch frequency.

In the current CIS-strategy, the envelope signals only are used for further processing, i.e., they contain the entire stimulation information. For each channel, the envelope is represented as a sequence of biphasic pulses at constant repetition rate. As a characteristic feature of CIS, this repetition rate (typically 1.5 kpps) is equal for all channels, and there is no relation to the center frequencies of the individual channels. It is intended that the repetition rate is not a temporal cue for the patient, i.e., it should be sufficiently high, so that the patient does not perceive tones with a frequency equal to the repetition rate. The repetition rate is usually set to more than twice the bandwidth of the envelope signals (Nyquist theorem).

Electrode Configuration of a 12-Channel Cochlear Implant Using Monopolar Stimulation FIG. 2 shows an example of an electrode configuration used in a 12-channel cochlear implant as described in U.S. Pat. No. 6,600,955. An electrode array containing 12 electrode contacts 201 (black dots) is positioned within the scala tympani of the cochlea. Each of these electrodes 201 is connected to a capacitor C 203 and a pair of current sources 205 and 207, whereby the second ports of current sources 205 and 207 are connected to implant ground GND 209 and implant supply voltage $V_{CC}$ 211, respectively. Current sources 205 and 207 may be implemented, for example, using P-channel and N-channel MOS field effect transistors, respectively. Thus, for convenience, the sources 205 and 207 are designated as P-sources and N-sources. Reference electrode 213 is positioned outside the cochlea and connected to a pair of switches 215 and 217, whereby the second ports of switches 215 and 217 are connected to implant ground GND and implant supply voltage $V_{CC}$, respectively.

A simplified lumped-element model of this configuration is shown in FIG. 3. Impedances $Z_I$ 301 represent the interface impedances between the metal surfaces of the intra-cochlear electrode contacts and the fluid within the scala tympani. Impedance $Z_{I,REF}$ 303 represents the interface impedance of the reference electrode. The intra-cochlear fluid is represented by the ohmic resistors $R_S$ 305. Since the cross-sectional area is changing along the scala tympani, usually a variable $R_S$ is assumed, as described in Kral A., Hartmann R., Mortazavi D., and Klinke R., "Spatial Resolution of Cochlear Implants: The Electrical Field and Excitation of Auditory Afferents," Hearing Research 121, pp. 11-28, 1998, which is hereby incorporated herein by reference. Resistors $R_B$ 307 describe the bony structures in which the cochlea is embedded, and they are also position-dependent. The spatial dependencies are of minor importance and therefore, for convenience, $R_S$ and $R_B$ are assumed to be constant. Besides, an infinite ladder network $R_S/R_B$ is assumed. The stimulation current passes the highly resistive structures on its way to the reference electrode.

Impedances $Z_I$ and $Z_{I,REF}$ in general are complex and frequency-dependent. However, in-vitro measurements of the impedances show that for the electrode geometries and the very short pulsatile stimulation waveforms used in cochlear implant applications, the interface impedances can be assumed to be purely ohmic.

As described in U.S. Pat. No. 6,600,955, a stimulation configuration as shown in FIG. 3 may be used to generate either (a) single non-simultaneous stimulation pulses, or (b) simultaneous pulses which are "sign-correlated". For example, the two phases of a single symmetric, biphasic pulse in one electrode are produced by first activating one of the P-sources 313 associated to this electrode and closing switch 315, and then activating the associated N-source 311 and closing switch 317. In the first phase of this pulse, the current is flowing from the pair of associated current sources via the ladder network to the pair of switches, and in the second phase the current direction is reversed. If current amplitudes and phase durations of the two phases are equal, the pulse is charge balanced, that is, no net charge is delivered to the ladder network.

If more than one stimulation pulses are applied simultaneously, such pulses are subject to "sign-correlation", i.e., either several P-sources are activated simultaneously and switch 315 is closed, or several N-sources are activated simultaneously and switch 317 is closed, but no mixture between activated P- and N-sources occurs. This ensures that the sum of currents is always flowing through the reference electrode (i.e., impedance $Z_{I,REF}$). Such a stimulation arrangement is designated as "distributed monopolar".

The electrical potentials which occur, for example, during the first phase of a single biphasic pulse are explained with the help of FIG. 4. Let P-source 401 produce a particular amplitude $I_P$ causing a voltage drop $U_P$ (note that the associated N-source 403 is inactive in this phase). Assuming capacitor 405 as being uncharged prior to the pulse, current $I_P$ will cause a voltage $U_C$ across capacitor 405, which is linearly increasing with time. However, assuming a sufficiently high capacitance, only a comparatively small voltage will drop across capacitor 405 the end of the first pulse phase. Typically, $U_C$ is not larger than some tens of millivolts, and thus is usually is negligible as compared to other voltage drops in the ohmic network. Interface impedance $Z_I$ causes a considerable voltage drop $U_I=Z_I I_P$. Current $I_P$ is distributed within the infinite ladder network composed of horizontal resistors $R_S$ and vertical resistors $R_B$. The distribution of voltage drops across vertical resistors $R_B$ will show exponential behavior, where the maximum voltage drop $U_B$ occurs in resistor 409, and the voltage drops across the neighboring resistors $R_B$ at both sides will decay exponentially, i.e., $\alpha U_B$ in resistors 411 and 413, $\alpha^2 U_B$ in resistors 415 and 417, $\alpha^3 U_B$ in resistors 419 and 421, etc. Factor $\alpha$ is a function of ratio $R_S/R_B$ only, and a short calculation yields $$\alpha = 1 + \frac{R_S}{2R_B} - \sqrt{\frac{R_S}{R_B} + \left(\frac{R_S}{2R_B}\right)^2}.$$

The sum of all currents flowing through resistors $R_B$ is again $I_P$, which is flowing back to implant ground via impedance $Z_{I,REF}$ 423 and the closed switch 425. Voltage $U_{I,REF}$ across $Z_{I,REF}$ is given by $U_{I,REF}=Z_{I,REF} I_P$, and assuming ideal switches, there is no voltage drop across the closed switch 425. Summing up all voltage drops yields the implant supply voltage $V_{CC}$, that is, $$V_{CC}=U_P+U_C+U_I+U_B+U_{I,REF}. \qquad (1)$$

The overall power consumption of such a circuit is $$P_{TOT}=V_{CC} I_P \qquad (2)$$

In the present application, $P_{TOT}$ is preferably as small as possible. For a given current amplitude $I_P$, the overall power consumption is minimized, if the implant supply voltage is minimized.

As a typical numeric example, assume interfaces impedances $Z_I=5$ k$\Omega$ and $Z_{I,REF}=250\Omega$, ladder network impedances $R_S=450\Omega$ and $R_B=9$ k$\Omega$ (resulting in $\alpha=0.8$), and a current amplitude $I_P=800$ µA. These assumptions yield $U_I=4$V, $U_B=0.8$V, and $U_{I,REF}=0.2$V. Inserting in Eq. (1) and neglecting voltage $U_C$ across the capacitor yields $V_{CC}-U_P=U_I+U_B+U_{I,REF}=5$V. Assuming that the P-source 401 can be operated with negligible voltage $U_P$ yields a minimum implant supply voltage $V_{CC}=5$V. Inserting in Eq. (2) yields overall power $P_{TOT}=4$ mW. Obviously, 80% of $P_{TOT}$ is absorbed by interface impedance $Z_I$, i.e., $P_I=U_I I_P=3.2$ mW, and this power does not contribute to the stimulation itself. Thus, any reduction of voltage drop $U_I$ is desirable with respect to both the reduction of the implant supply voltage and the reduction of the stimulation power consumption.

One approach for reducing the voltage drop across $Z_I$ is to try to reduce $Z_I$ itself. For example, using larger electrode surfaces would reduce $Z_I$. However, the size of the electrode surfaces typically cannot be increased further, because geometrical limits such as electrode distances have already been reached. Another approach is based on the observation that $Z_I$ is not stable over time, but increasing in the weeks after the implantation. The reasoning is that the growth of a particular tissue covers the electrode surfaces. Giving corticoids during surgery seems to reduce this additional tissue growth and keep the impedance at least at its initial value.

SUMMARY OF THE INVENTION

In a first aspect of the invention, a method is provided for simultaneously activating electrodes in a multi-channel electrode array having a monopolar electrode configuration. The method includes determining a desired potential for a given position relative to the electrode array. Amplitudes of simultaneous, sign-correlated pulses associated with at least two electrodes of the multi-channel array are determined so as to provide a total potential at the given position that is substantially equal to the desired potential. The at least two electrodes are simultaneously activated as a function of the determined amplitudes to achieve the desired potential at the given position, wherein the at least two electrodes have spatial channel interaction when activated.

In accordance with related embodiments of the invention, determining amplitudes may include adding a resulting potential from each of the sign-correlated pulses at the given position. Each of the determined amplitudes may be less than the amplitude needed to activate an electrode in the multi-channel electrode array using a continuous-interleaved-sampling strategy to achieve the desired potential. The power required to activate the at least two electrodes using the simultaneous, sign-correlated pulses may be less than the power needed to activate the at least two electrodes in the multi-channel array using a continuous-interleaved-sampling strategy to achieve the desired potential. The electrode array may be implanted into a living subject. For example, the electrode array may be used to stimulate the acoustic nerve.

In another aspect of the invention, a method of activating electrodes in a multi-channel electrode array includes determining a sequential stimulation sequence having a sequential stimulation sequence pulse rate and sequential stimulation sequence mean pulse amplitude, the sequential stimulation sequence for producing desired potentials at given positions relative to the multi-channel electrode array. The sequential stimulation sequence, which may be, for example, a continuous-interleaved-sampling (CIS) sequence, is converted to a channel interaction (CI) sequence using simultaneous, sign-correlated pulses and channel interaction compensation. The CI sequence has a CI pulse rate and a CI mean pulse amplitude, the CI sequence for producing resulting potentials that are substantially equal to the desired potentials at the given positions.

In accordance with related embodiments of the invention, the electrodes may then be activated as a function of the CI sequence. The mean pulse amplitude for the CI sequence may be less than the mean pulse amplitude for the sequential stimulation sequence. The stimulation power required for the CI sequence may be less than the stimulation power required for the sequential stimulation sequence. The sequential stimulation sequence and/or the CI sequence may include symmetrical biphasic current pulses. The multi-channel array may use a monopolar electrode configuration having a remote ground.

In accordance with further embodiments of the invention, the CI pulse rate may be substantially equal to the sequential stimulation sequence pulse rate, such that the CI sequence includes temporal gaps between pulses. The CI pulse rate may be increased, wherein the temporal gap between pulses is decreased. The pulse amplitude of the CI sequence may be reduced while increasing pulse phase duration such that charge per pulse remains substantially unchanged, wherein the temporal gap between pulses is decreased.

In yet another aspect of the invention, a cochlear prosthesis system includes a stimulator adapted to be implantable, the stimulator including a multi-channel electrode array having a monopolar electrode configuration. A processor is operatively coupled to the stimulator. The processor is configured to determine amplitudes of simultaneous, sign-correlated pulses associated with at least two electrodes of the multi-channel array such that a total potential at a given position relative to the multi-channel electrode array equals a desired potential, the at least two electrodes having spatial channel interaction. The processor is further configured to simultaneously activate the at least two electrodes as a function of the determined amplitudes to achieve the desired potential at the given position.

In accordance with related embodiments of the invention, the total potential equals the summation of the resulting potentials from each of the simultaneous, sign-correlated pulses at the given position. Each of the determined amplitudes may be less than a pulse amplitude needed to activate an electrode in the multi-channel electrode array using a continuous-interleaved-sampling strategy to achieve the desired potential at the given position. The power required to simultaneously activate the at least two electrodes using the sign-correlated pulses may be less than the power needed to activate the at least two electrodes using a continuous-interleaved-sampling strategy to achieve desired potentials.

In still another aspect of the invention, a cochlear prosthesis system includes a stimulator adapted to be implantable, the stimulator including a multi-channel electrode array having a monopolar electrode configuration. A processor is operatively coupled to the stimulator. The processor is configured to determine a sequential stimulation sequence having a sequential stimulation sequence pulse rate and sequential stimulation sequence mean pulse amplitude, such that desired potentials are produced at given positions relative to the multi-channel electrode array. Furthermore, the processor converts the sequential stimulation sequence to a channel interaction (CI) sequence using simultaneous, sign-correlated pulses and channel interaction compensation, the CI sequence having a CI pulse rate and a CI mean pulse amplitude, the CI sequence for producing resulting potentials that are substantially equal to the desired potentials at the given positions.

In accordance with related embodiments of the invention, the processor may be configured to simultaneously activate at least two electrodes of the multi-channel electrode array as a function of the CI sequence to achieve the desired potential at the given position. The mean pulse amplitude for the CI sequence may be less than the mean pulse amplitude of the sequential stimulation sequence. The stimulation power required for the CI sequence may be less than the stimulation power required by the sequential stimulation sequence. The sequential stimulation sequence and the CI sequence may include symmetrical biphasic current pulses. The CI pulse rate may be substantially equal to the sequential stimulation sequence pulse rate, such that the CI sequence includes temporal gaps between pulses. The processor may be further configured to increase the CI pulse rate, wherein the temporal gap between pulses is decreased. The processor may be further configured to reduce the pulse amplitude of the CI sequence while increasing pulse phase duration such that charge per pulse remains substantially unchanged, wherein the temporal gap between pulses is decreased. The sequential stimulation sequence may be a continuous-interleaved-sampling (CIS) sequence.

In another aspect of the invention, a stimulation system includes a stimulator including a multi-channel electrode array having a monopolar electrode configuration. A processor is operatively coupled to the stimulator. The processor is configured to determine a channel interaction (CI) sequence using simultaneous, sign-correlated pulses and channel interaction compensation, the CI sequence having a CI pulse rate and a CI mean pulse amplitude. The CI sequence for producing resulting potentials that are substantially equal to desired potentials at given positions relative to the multi-channel array.

In accordance with related embodiments of the invention, the stimulator may be adapted to be implantable, and may be part of a cochlear implant. The processor may be configured to simultaneously activate at least two electrodes of the multi-channel electrode array as a function of the CI sequence to achieve the desired potential at the given position. The CI sequence may include symmetrical biphasic current pulses.

In accordance with further related embodiments of the invention, the CI sequence may include temporal gaps between pulses. The processor may be further configured to increase the CI pulse rate, such that the temporal gap between pulses is decreased. The processor may be further configured to reduce the pulse amplitude of the CI sequence while increasing pulse phase duration, such that charge per pulse remains substantially unchanged and the temporal gap between pulses is decreased.

In still another aspect of the invention, a stimulation system includes a stimulator including a multi-channel electrode array having a monopolar electrode configuration. A control means controls the stimulator. The control means determines a channel interaction (CI) sequence using simultaneous, sign-correlated pulses and channel interaction compensation. The CI sequence has a CI pulse rate and a CI mean pulse amplitude, and produces resulting potentials that are substantially equal to desired potentials at given positions relative to the multi-channel array.

In accordance with related embodiments of the invention, the stimulator may be adapted to be implantable, and may be part of a cochlear implant. The control means may simultaneously activate at least two electrodes of the multi-channel electrode array as a function of the CI sequence to achieve the desired potential at the given position. The CI sequence includes symmetrical biphasic current pulses.

In accordance with further related embodiments of the invention, the CI sequence may include temporal gaps between pulses. The control means may increase the CI pulse rate, such that the temporal gap between pulses is decreased. The control means may be further configured to reduce the pulse amplitude of the CI sequence while increasing pulse phase duration, such that charge per pulse remains substantially unchanged and the temporal gap between pulses is decreased.

In yet another aspect of the invention, a computer program product is provided for simultaneously activating electrodes in a multi-channel electrode array having a monopolar electrode configuration. The computer program product includes a computer usable medium having computer readable program code thereon. The computer readable program code includes program code for determining a channel interaction (CI) sequence using simultaneous, sign-correlated pulses and channel interaction compensation, the CI sequence having a CI pulse rate and a CI mean pulse amplitude, the CI sequence for producing resulting potentials that are substantially equal to a desired potentials at given positions relative to the multi-channel array.

In accordance with further related embodiments, the computer program product further comprises program code for simultaneously activating at least two electrodes of the multi-channel electrode array as a function of the CI sequence to achieve the desired potential at the given position. The CI sequence may include symmetrical biphasic current pulses.

In accordance with still further embodiments of the invention, the CI sequence includes temporal gaps between pulses. The computer product may further include program code for increasing the CI pulse rate such that the temporal gap between pulses is decreased. The computer program product may further include program code for reducing the pulse amplitude of the CI sequence while increasing pulse phase duration, such that charge per pulse remains substantially unchanged and the temporal gap between pulses is decreased.

BRIEF DESCRIPTION OF THE DRAWINGS

The foregoing features of the invention will be more readily understood by reference to the following detailed description, taken with reference to the accompanying drawings, in which:

FIG. 5a shows two (normalized) scala tympani potentials due to two sequentially applied stimulation pulses of equal amplitudes;

FIG. 5b shows two (normalized) scala tympani potentials due to two CIC stimulation pulses applied simultaneously, in accordance with an embodiment of the invention;

FIG. 6(a) shows sequential pulses in conventional CIS;

FIG. 6(b) shows simultaneous pulses in a CI sequence, in accordance with an embodiment of the invention;

FIG. 6(c) shows the CI sequence of FIG. 6(b) with increased pulse phase duration, in accordance with an embodiment of the invention;

DETAILED DESCRIPTION OF SPECIFIC EMBODIMENTS

In illustrative embodiments, a system and method for simultaneously activating electrodes in a multi-channel electrode array is presented. A simultaneous stimulation sequence, such as a channel interaction (CI) sequence having simultaneous, sign-correlated pulses and channel interaction compensation, includes temporal gaps between pulses. The CI sequence may be, for example, based on a sequential stimulation sequence such that the CI pulse rate is substantially equal to the sequential stimulation sequence pulse rate. For implementation of "fine structure strategies," the CI pulse rate is increased by filling the temporal gaps between pulses with additional pulses, such that the information rate is increased. In other embodiments, the pulse amplitudes of the CI sequence may be reduced without increasing the number of pulses per second, allowing for low power and low voltage implementations of standard sequential stimulation strategies. Details of illustrative embodiments are discussed below.

Simultaneous Stimulation

Figure 3:
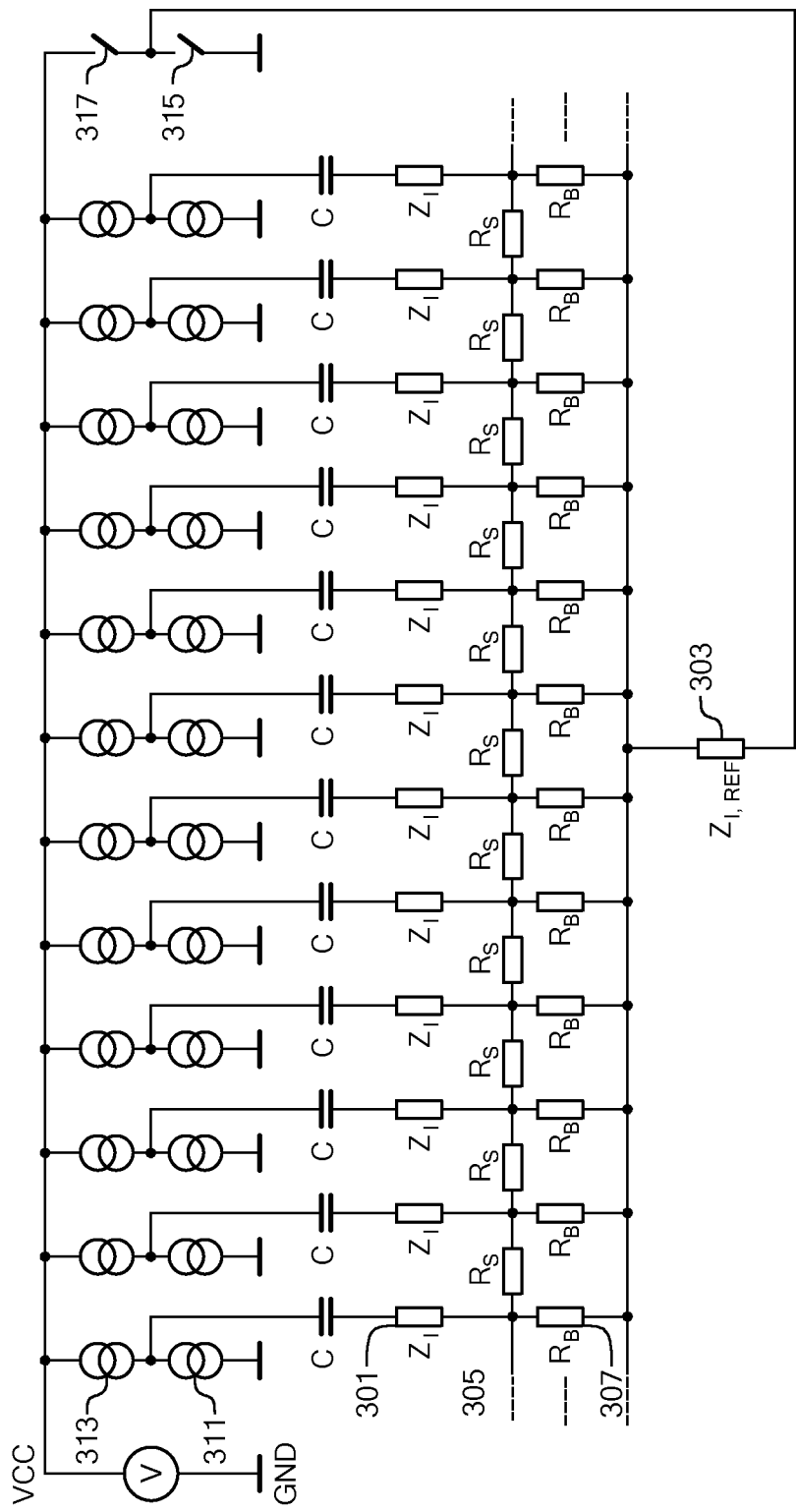
FIG. 3 shows a simplified lumped-element model of the electrode configuration of FIG. 2.
Figure 4:
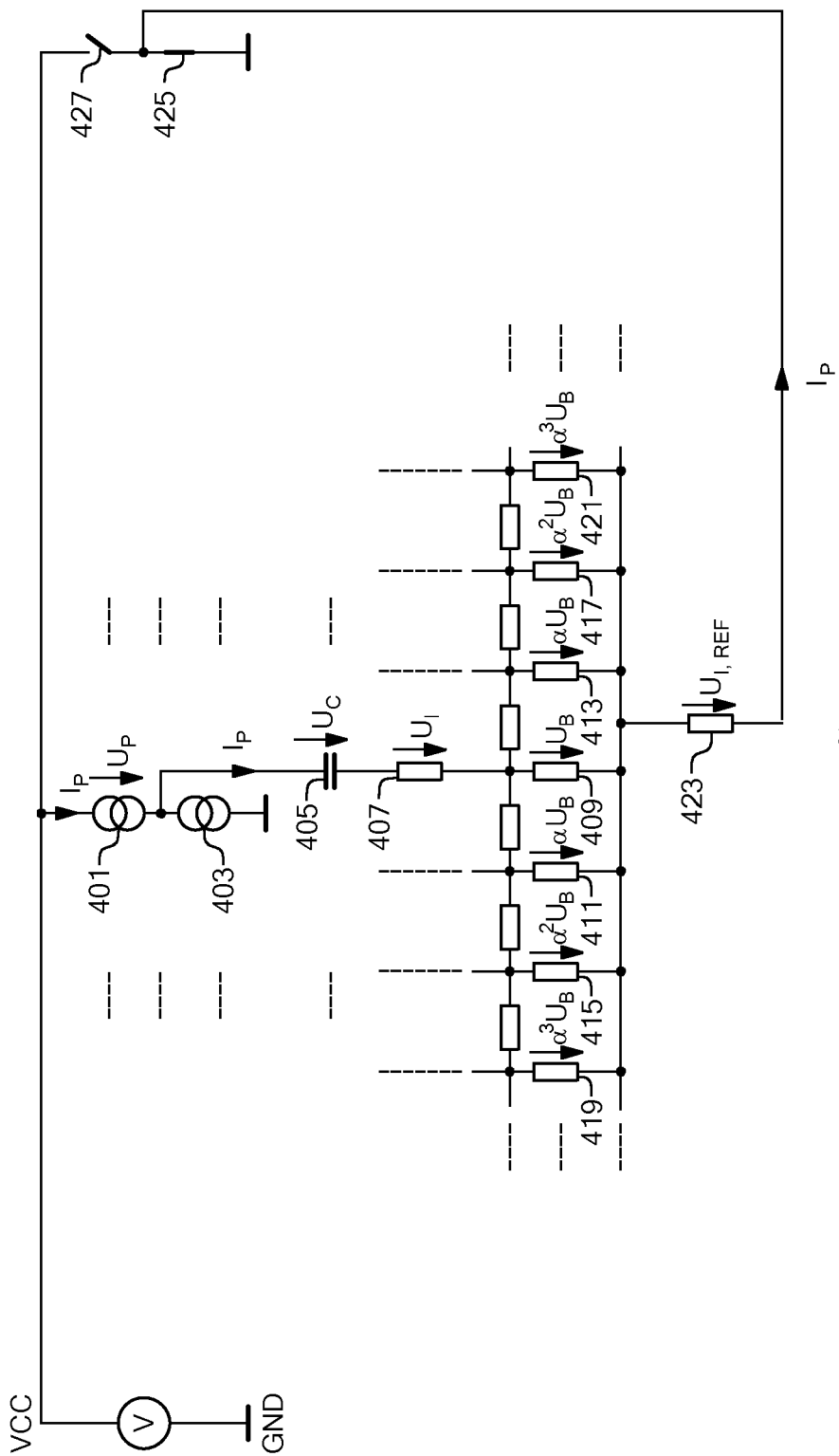
FIG. 4 shows details of electrical currents and voltages of FIG. 2, when one phase of a stimulation pulse is elicited.

Referring to FIG. 3, the voltage drop across interface impedances $Z_I$ is reduced based on simultaneous stimulation of two or more channels. If two or more electrodes are stimulated simultaneously, then effects of spatial channel interaction can be exploited, as described below.

a. Spatial Channel Interaction

Spatial channel interaction occurs when different stimulation electrodes (positioned in the scala tympani) are activated and there is considerable geometric overlapping of electrical fields at the location of the excitable nerve tissue. Thus the same neurons are activated, if different electrodes are stimulated. Stimulation of a particular electrode against a remote ground electrode (monopolar stimulation) causes an electrical potential within the scala tympani which can roughly be described by two decaying exponentials at both sides of the electrode, and the space constant (in humans) is typically $\lambda \approx 10$ mm.

In the CIS strategy, the influence of spatial channel interaction is reduced by employing pulses which are not overlapping in time (interleaved sampling). The conductivity in the scala tympani here leads to a considerable spread and a defocusing of the electrical field at the site of the excitable tissue. However, an additional effect occurs, if uncorrelated simultaneous stimulation of two or more electrodes against a remote ground electrode is considered. Here the conductivity represents a shunt conductance between active electrodes, which in general results in a mixture of constructive and destructive superposition of electrical fields at the position of the neurons. For example, if two simultaneous stimulation channels produce currents with equal amplitudes, but different signs, most of the current will flow through the shunt conductance and will not reach the intended neurons.

b. Sign-Correlated Pulses

Preferred embodiments of the invention utilize the simultaneous activation of two or more electrodes in the scala tympani against a remote reference electrode (monopolar electrode configuration). Furthermore, all pulses are exactly simultaneous, that is, positive and negative pulse-phases start and stop at the same time instants, respectively. In addition, all simultaneous phases have the same sign. As used herein, such simultaneous pulses are designated as "sign-correlated" pulses.

Employing sign-correlated pulses ensures that the sum of the single stimulation currents is always flowing through the reference electrode. Thus, at the site of the excitable neurons only constructive superposition of currents occurs.

c. Channel Interaction Compensation (CIC)

"Channel interaction compensation (CIC)" as described in U.S. Pat. No. 6,594,525, is used to convert a set of sequential amplitudes into a set of simultaneous amplitudes, whereby the potentials within the scala tympani at the position of the activated electrodes are unchanged. An example using two electrodes is illustrated in FIG. 5(a-b). FIG. 5(a) (prior art) shows two (normalized) scala tympani potentials due to two sequentially applied stimulation pulses of equal amplitudes. The distance between the active electrodes is 12 mm. Each potential distribution shows exponential decays with $\lambda=10$ mm at both sides. FIG. 5(b) shows the resulting potential (solid line), if two stimulation pulses are applied simultaneously and after the amplitudes have been adapted using CIC, in accordance with an embodiment of the invention. Note that the peak potentials at the position of the electrodes have not been changed as compared to the upper plot. This curve is the result of the superposition of the two single potentials (dotted lines). Regarding the maximum amplitudes of the single potentials, it is clear that these are reduced as compared to the potentials of the FIG. 5(a). In this example, the reduction is 23%.

Reduction of Stimulation Power a. Reduction of Stimulation Power Using Simulataneous Stimulation As a general feature of CIC, by taking into account spatial channel interaction, the stimulation pulse amplitudes are reduced. Thus, any stimulation strategy utilizing simultaneous stimulation in combination with CIC leads to an average reduction of stimulation power, if such a strategy is compared to standard CIS using the same number of stimulation pulses per second. The amount of average reduction depends on a variety of parameters, such as the number of channels used simultaneously, the distance between these channels, or the spatial decay constants. The amount of average reduction also depends on the probability distribution of the sequential amplitudes used as an input to CIC. Referring back to the example shown in FIGS. 5(a-b), the power consumption is reduced proportional to the reduction of the stimulation amplitudes, that is by 23%. However, the case of two equal sequential amplitudes represents the "best case" with respect to power saving effects. The "worst case" occurs, if one of the two sequential amplitudes is zero. Then CIC does not change these amplitudes, and therefore there is no power saving.

For example, consider a 6-channel intra-cochlear electrode array, where the distance between adjacent electrodes is 4 mm. Driven in standard CIS-mode, pulses occur strictly sequentially, for example, following the pattern . . . (1) (2) (3) (4) (5) (6) (1) (2) . . . , as shown in FIG. 6(a). A CIC-based system is shown in FIG. 6(b), in accordance with an embodiment of the invention. In FIG. 6(b), simultaneous, sign-correlated pulses occur. More particularly, each of the three electrode pairs (1,4), (2,5), and (3,6) are simultaneous, following the pattern, without limitation, of . . . (1,4) (2,5) (3,6) (1,4) . . . . The decay constant may be, for example, $\lambda=10$ mm. FIG. 5(b) represents an example for such an electrode pair. Assuming that both systems utilize the same number of stimulation pulses per second and both systems use the same implant supply voltage, an average reduction of simulation power in the range of by $\approx 15$-$20\%$ can be expected.

b. Reduction by Using Longer Pulses

As shown in FIG. 6b, applying simultaneous pulses introduces a gap between pairs of simultaneous pulses. In case of using, without limitation, two pulses simultaneously, this gap can be closed by doubling the phase durations, as shown in FIG. 6c in accordance with an embodiment of the invention. For equal charge per phase, the stimulation amplitude can be reduced by a factor 2. For N simultaneous pulses, the phase durations of sequential pulses can be multiplied by N, and for equal charge per phase, the amplitudes can be divided by a factor N. This reduction in amplitudes can be exploited for a reduction of the implant supply voltage $V_{CC}$, that is, the implant supply voltage can be divided by N. Since the same charge per phase is used as for simultaneous pulses with short phases, the overall stimulation power being proportional to the product of implant supply voltage and the mean stimulation amplitude is reduced by a factor N.

Both the reduction of stimulation power and the reduction of the implant supply voltage represents substantial advantages, in particular with respect to a totally implantable cochlear implant (TICI). Whereas a low power consumption is a general advantage with respect to the limited power resources in a TICI, there is a particular interest in low-voltage stimulation strategies, where stimulation runs at very low implant supply voltages down to $V_{CC}=3V$. In contemporary cochlear implants, the implant supply voltage is typically about $V_{CC}=5$-$6V$. If low-voltage stimulation strategies are applied, then the voltage produced by rechargeable batteries can directly be used directly. For example, lithium polymer secondary batteries using lithium cobalt oxide ($LiCoO_2$) produce 3.65V. Such a supply voltage would not be sufficient for the implementation of the standard CIS-strategy. Therefore voltage doubling or similar circuits are necessary, and such circuits considerably increase size and power consumption of a TICI.

Figure 1:
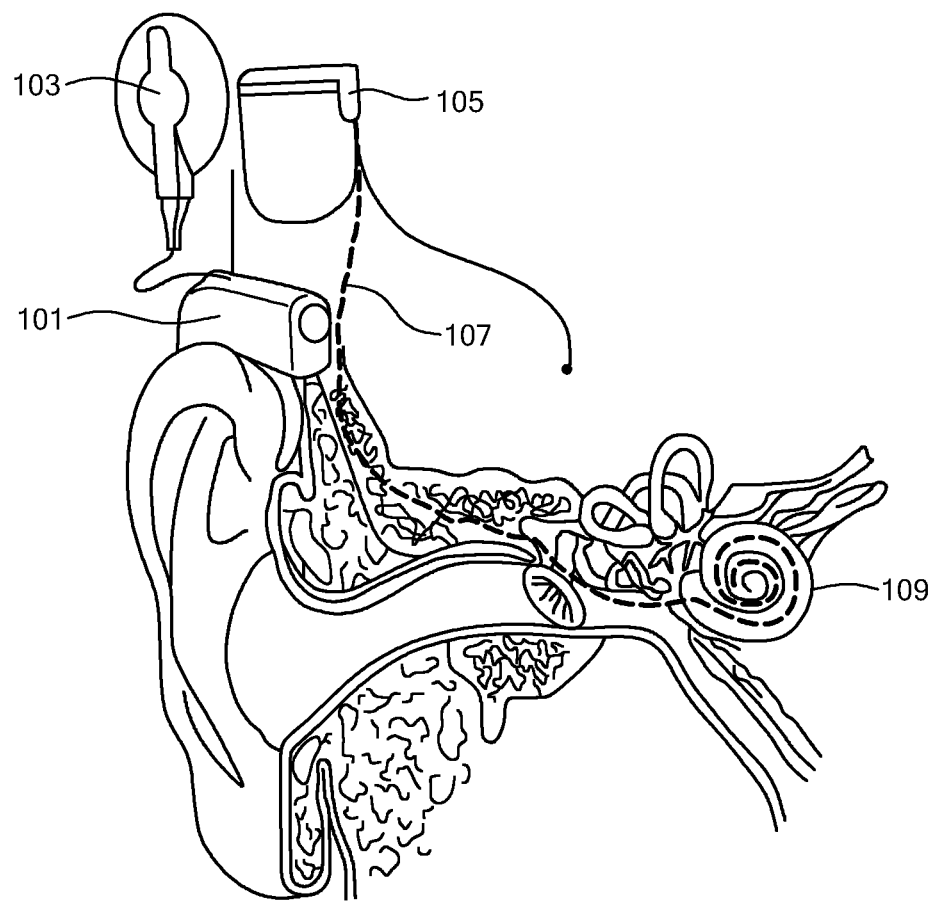
FIG. 1 shows a conventional cochlear prosthesis.
Figure 2:
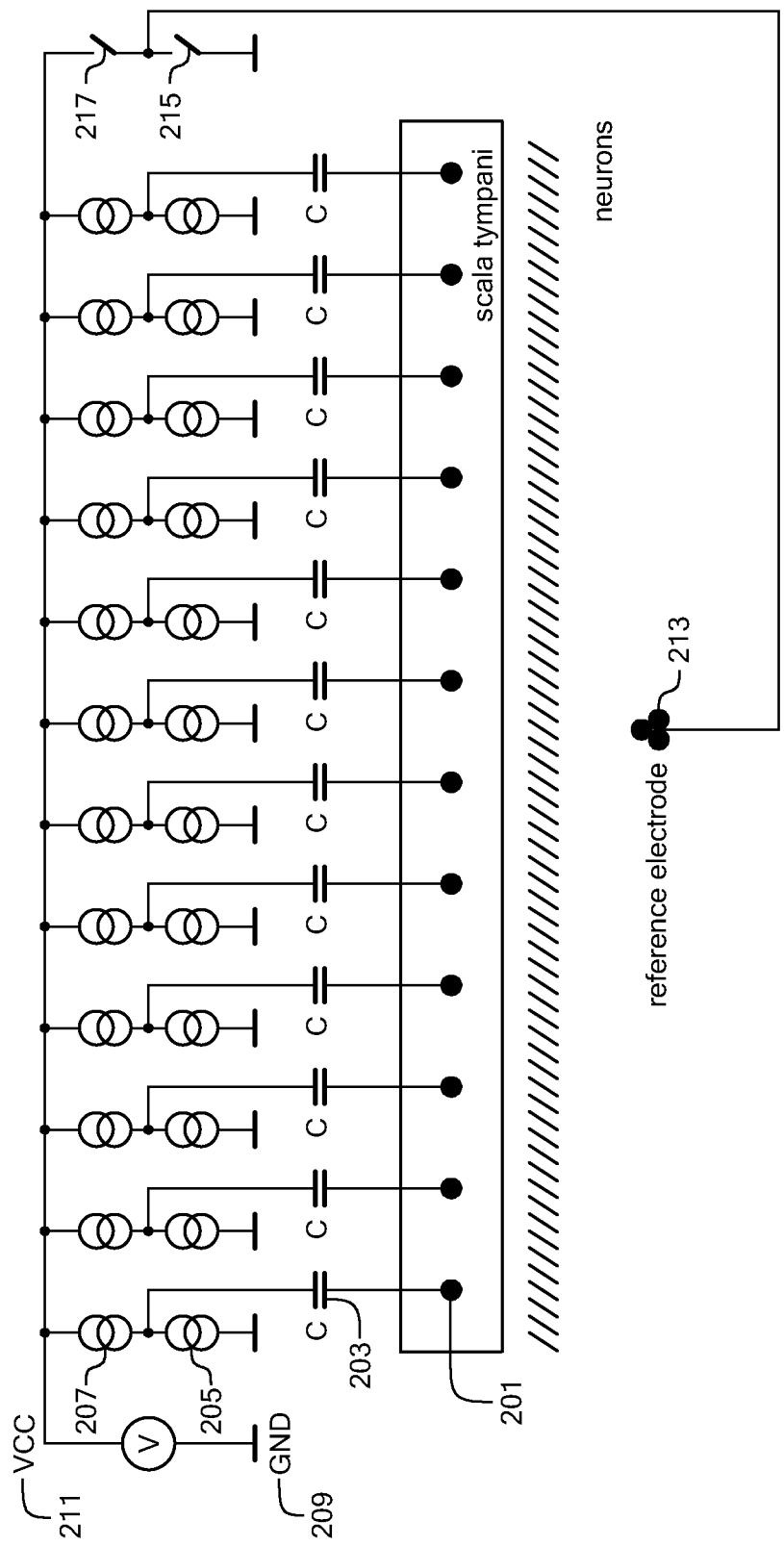
FIG. 2 shows a block diagram of a monopolar electrode configuration used in a 12-channel cochlear implant.
Figure 7:
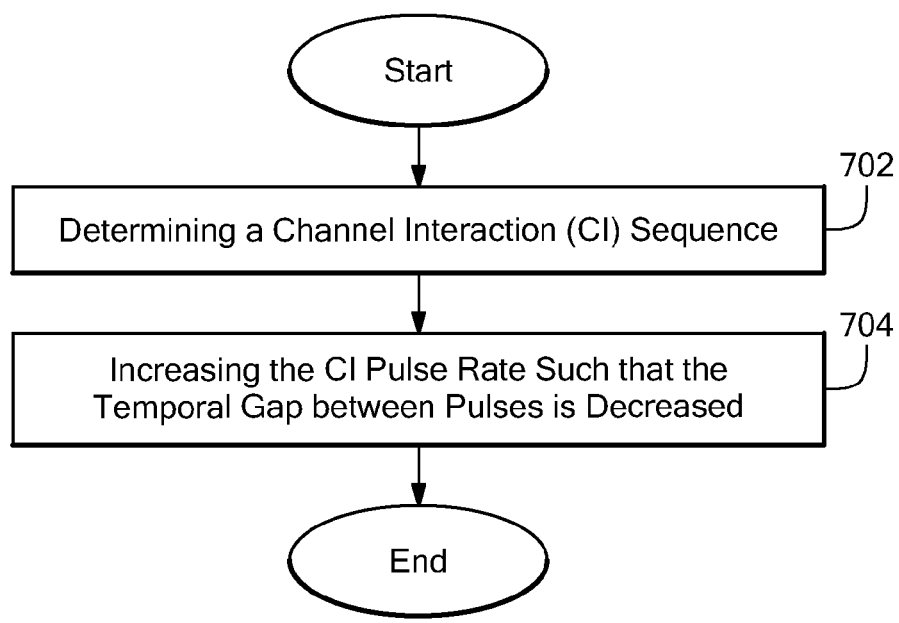
FIG. 7 shows a method of increasing the stimulation information rate, in accordance with an embodiment of the invention.

In illustrative embodiments of the invention, applying simultaneous stimulation using sign-correlated pulses in combination with CIC can be exploited to increase the information rate, for example, in applying "fine structure" stimulation strategies. FIG. 7 shows a method of increasing the stimulation information rate, in accordance with various embodiments of the invention. The method may be implemented, without limitation, by a stimulation system that includes: a stimulator 105 having a multi-channel electrode array 107 utilizing a monopolar electrode configuration; and a controller, such as processor 101 for controlling the stimulator 105, as shown in FIG. 1. Controller may include, without limitation, various circuitry, and/or memory and be appropriately pre-programmed or configured to be loaded with an appropriate program. Memory may include, for example, a diskette, a fixed disk, a Compact Disk (CD), Read Only Memory (ROM), Erasable Programmable Read-Only Memory (EPROM), and/or Random Access Memory (RAM). As shown in FIG. 1, various parts of the system may be implantable, and may be part of a cochlear implant that stimulates the acoustic nerve.

In step 702 of FIG. 7, the controller determines a channel interaction (CI) sequence using simultaneous, sign-correlated pulses and channel interaction compensation. As described above, the CI sequence has a CI pulse rate and a CI mean pulse amplitude, and produces resulting potentials that are substantially equal to desired potentials at given positions relative to the multi-channel array.

In various embodiments of the invention, the controller determines the CI sequence by determining a sequential stimulation sequence, such as a CIS sequence, having a sequential stimulation sequence pulse rate and sequential stimulation sequence mean pulse amplitude for producing desired potentials at given positions relative to the multi-channel electrode array. The controller then converts the sequential stimulation sequence into a channel interaction (CI) sequence that uses simultaneous, sign-correlated pulses and channel interaction compensation, so as to produce resulting potentials that are substantially equal to the desired potentials at the given positions. As noted above, each of the CI pulse amplitudes is typically less than the amplitude needed to activate an electrode in the multi-channel electrode array using the sequential stimulation sequence, as simultaneous CI pulses are added to produce the desired potentials.

Such a converted CI sequence, or an initially determined CI sequence, may include temporal gaps between pulses. This can be advantageously exploited by the controller, for example, by increasing the CI pulse rate such that the temporal gap between pulses is decreased, as shown in step 704 of FIG. 7. The increased stimulation rate allows for implantation of fine structure stimulation strategies, as described above. Based on the CI sequence, the controller then simultaneously activates at least two electrodes as a function of the determined CI pulse amplitudes to achieve, via spatial channel interaction, the desired potential at the given position.

Figure 8:
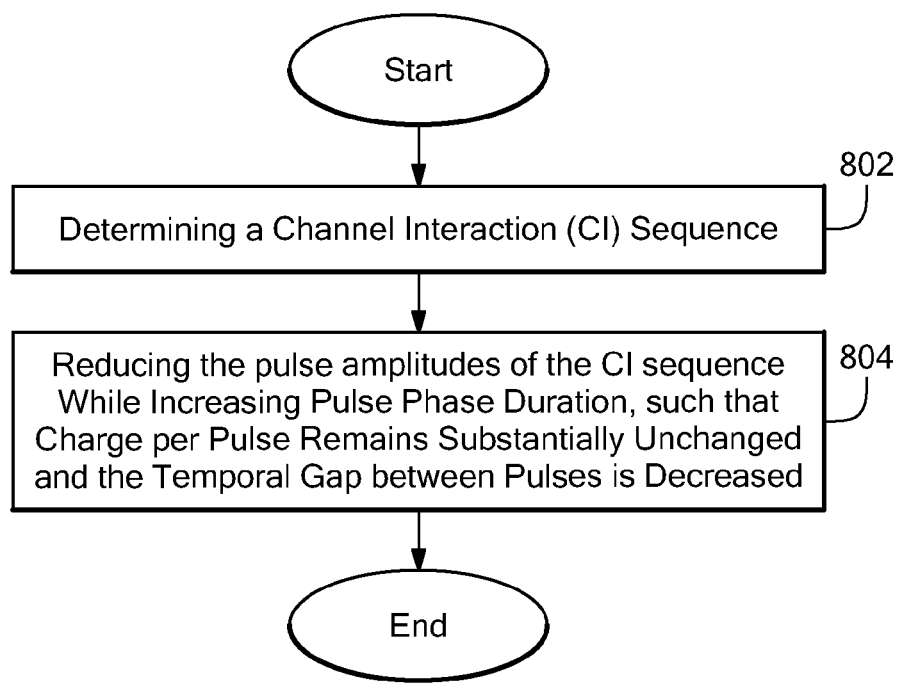
FIG. 8 shows a method of decreasing stimulation power and voltage requirements, in accordance with an embodiment of the invention.

As described above, in various embodiments the temporal gap between pulses may also be advantageously exploited to allow for low-power and low-voltage implementations of standard CIS-stimulation strategies. FIG. 8 shows a method of decreasing stimulation power and voltage requirements, in accordance with various embodiments of the invention. In step 802 of FIG. 8, the controller determines a channel interaction (CI) sequence using simultaneous, sign-correlated pulses and channel interaction compensation, similar to step 703 in FIG. 7. In step 804 of FIG. 8, the pulse amplitudes of the CI sequence are reduced while increasing pulse phase duration, such that charge per pulse remains substantially unchanged and the temporal gap between pulses is decreased.

In various embodiments, the disclosed method may be implemented as a computer program product for use with a computer system. Such implementation may include a series of computer instructions fixed either on a tangible medium, such as a computer readable media (e.g., a diskette, CD-ROM, ROM, or fixed disk) or transmittable to a computer system, via a modem or other interface device, such as a communications adapter connected to a network over a medium. Medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable media with accompanying printed or electronic documentation (e.g., shrink wrapped software), preloaded with a computer system (e.g., on system ROM or fixed disk), or distributed from a server or electronic bulletin board over the network (e.g., the Internet or World Wide Web).

Although various exemplary embodiments of the invention have been disclosed, it should be apparent to those skilled in the art that various changes and modifications can be made which will achieve some of the advantages of the invention without departing from the true scope of the invention. These and other obvious modifications are intended to be covered by the appended claims.

What is claimed is:

1. A method of activating electrodes in a multi-channel electrode array, the method comprising:
   determining a sequential stimulation sequence having a sequential stimulation sequence pulse rate and sequential stimulation sequence mean pulse amplitude, the sequential stimulation sequence for producing desired potentials at given positions relative to the multi-channel electrode array; and
   converting the sequential stimulation sequence to a channel interaction (CI) sequence using simultaneous, sign-correlated pulses and channel interaction compensation, the CI sequence having a CI pulse rate and a CI mean pulse amplitude, the CI sequence for producing resulting potentials that are substantially equal to the desired potentials at the given positions.

2. The method according to claim 1, further comprising activating electrodes in the multi-channel array as a function of the CI sequence.

3. The method according to claim 1, wherein the mean pulse amplitude for the CI sequence is less than the mean pulse amplitude for the sequential stimulation sequence.

4. The method according to claim 1, wherein the stimulation power required for the CI sequence is less than the stimulation power required for the sequential stimulation sequence.

5. The method according to claim 1, wherein the sequential stimulation sequence and the CI sequence include symmetrical biphasic current pulses.

6. The method according to claim 1, wherein the multi-channel array uses a monopolar electrode configuration having a remote ground.

7. The method according to claim 1, wherein the CI pulse rate is substantially equal to the sequential stimulation sequence pulse rate, such that the CI sequence includes temporal gaps between pulses.

8. The method according to claim 7, further comprising increasing the CI pulse rate, wherein the temporal gap between pulses is decreased.

9. The method according to claim 7, further comprising reducing pulse amplitude of the CI sequence while increasing pulse phase duration such that charge per pulse remains substantially unchanged, wherein the temporal gap between pulses is decreased.

10. The method according to claim 1, wherein the sequential stimulation sequence is a continuous-interleaved-sampling (CIS) sequence.

11. A cochlear prosthesis system comprising:
a stimulator adapted to be implantable, the stimulator including a multi-channel electrode array having a monopolar electrode configuration;
a processor operatively coupled to the stimulator, the processor configured to:
determining a sequential stimulation sequence having a sequential stimulation sequence pulse rate and sequential stimulation sequence mean pulse amplitude, the sequential stimulation sequence for producing desired potentials at given positions relative to the multi-channel electrode array; and
converting the sequential stimulation sequence to a channel interaction (CI) sequence using simultaneous, sign-correlated pulses and channel interaction compensation, the CI sequence having a CI pulse rate and a CI mean pulse amplitude, the CI sequence for producing resulting potentials that are substantially equal to the desired potentials at the given positions.

12. The system according to claim 11, wherein the processor is configured to simultaneously activate at least two electrodes of the multi-channel electrode array as a function of the CI sequence to achieve the desired potential at the given position.

13. The system according to claim 11, wherein the mean pulse amplitude for the CI sequence is less than the mean pulse amplitude for the sequential stimulation sequence.

14. The system according to claim 11, wherein the stimulation power required for the CI sequence is less than the stimulation power required for the sequential stimulation sequence.

15. The system according to claim 11, wherein the sequential stimulation sequence and the CI sequence include symmetrical biphasic current pulses.

16. The system according to claim 11, wherein the CI pulse rate is substantially equal to the sequential stimulation sequence pulse rate, such that the CI sequence includes temporal gaps between pulses.

17. The system according to claim 16, wherein the processor is further configured to increase the CI pulse rate, wherein the temporal gap between pulses is decreased.

18. The system according to claim 16, wherein the processor is further configured to reduce the pulse amplitude of the CI sequence while increasing pulse phase duration, such that charge per pulse remains substantially unchanged, wherein the temporal gap between pulses is decreased.

19. The system according to claim 11, wherein the sequential stimulation sequence is a continuous-interleaved-sampling (CIS) sequence.

20. A stimulation system comprising:
a stimulator including a multi-channel electrode array having a monopolar electrode configuration;
a processor operatively coupled to the stimulator, the processor configured to determine a channel interaction (CI) sequence using simultaneous, sign-correlated pulses and channel interaction compensation, the CI sequence having a CI pulse rate and a CI mean pulse amplitude, the CI sequence for producing resulting potentials that are substantially equal to a desired potentials at given positions relative to the multi-channel array.

21. The system according to claim 20, wherein the stimulator is part of a cochlear implant.

22. The system according to claim 20, wherein the processor is configured to simultaneously activate at least two electrodes of the multi-channel electrode array as a function of the CI sequence to achieve the desired potential at the given position.

23. The system according to claim 20, wherein the CI sequence include symmetrical biphasic current pulses.

24. The system according to claim 20, wherein the CI sequence includes temporal gaps between pulses.

25. The system according to claim 24, wherein the processor is further configured to increase the CI pulse rate, such that the temporal gap between pulses is decreased.

26. The system according to claim 24, wherein the processor is further configured to reduce the pulse amplitude of the CI sequence while increasing pulse phase duration, such that charge per pulse remains substantially unchanged and the temporal gap between pulses is decreased.

27. A computer program product for simultaneously activating electrodes in a multi-channel electrode array having a monopolar electrode configuration, the computer program product comprising a non-transitory computer usable medium having computer readable program code thereon, the computer readable program code comprising:
program code for determining a channel interaction (CI) sequence using simultaneous, sign-correlated pulses and channel interaction compensation, the CI sequence having a CI pulse rate and a CI mean pulse amplitude, the CI sequence for producing resulting potentials that are substantially equal to a desired potentials at given positions relative to the multi-channel array.

28. The computer program product according to claim 27, further comprising program code for simultaneously activating at least two electrodes of the multi-channel electrode array as a function of the CI sequence to achieve the desired potential at the given position.

29. The computer program product according to claim 27, wherein the CI sequence includes temporal gaps between pulses.

30. The computer program product according to claim 29, further including program code for increasing the CI pulse rate such that the temporal gap between pulses is decreased.

31. The computer program product according to claim 29, further comprising program code for reducing the pulse amplitude of the CI sequence while increasing pulse phase duration, such that charge per pulse remains substantially unchanged and the temporal gap between pulses is decreased.

* * * * *